United States Patent [19]

Hatfield, Jr.

[11] Patent Number: 4,465,639
[45] Date of Patent: Aug. 14, 1984

[54] PROCESS FOR POLYISOCYANATES

[75] Inventor: Richard Hatfield, Jr., Pasadena, Tex.

[73] Assignee: The Upjohn Company, Kalamazoo, Mich.

[21] Appl. No.: 461,247

[22] Filed: Jan. 26, 1983

[51] Int. Cl.$^3$ ................. C07C 118/02; C07C 119/048
[52] U.S. Cl. ...................... 260/453 PH; 260/453 AM; 521/160
[58] Field of Search ................. 260/453 PH, 453 AM

[56] References Cited

U.S. PATENT DOCUMENTS

| | | | |
|---|---|---|---|
| 3,179,680 | 4/1965 | Kober | 260/453 SP |
| 3,526,652 | 1/1970 | Powers | 260/453 AM |
| 3,636,030 | 1/1972 | Perkins | 260/453 SP |
| 3,641,094 | 2/1972 | Arlt et al. | 260/453 PH |
| 4,221,877 | 9/1980 | Cuscurida et al. | 521/160 |

Primary Examiner—Dolph H. Torrence
Attorney, Agent, or Firm—Denis A. Firth; Robert A. Armitage

[57] ABSTRACT

Addition of controlled amounts of water to the reaction mixture produced by phosgenation of a mixture of polymethylene polyphenyl polyamines (and like polyamines produced by condensation of formaldehyde and aromatic amines) prior to complete removal of excess phosgene gives rise to the corresponding polymethylene polyphenyl polyisocyanates having significantly improved properties. Not only is the color of the product, and of polyurethane foams prepared therefrom, significantly lighter but the proportion of higher molecular weight products is significantly less and the viscosity is less. No undesirable by-products are introduced into the polyisocyanate as a result of the process.

11 Claims, No Drawings

PROCESS FOR POLYISOCYANATES

BACKGROUND OF THE INVENTION

1. Field of the Invention

This invention relates to the preparation of polyisocyanates and is more particularly concerned with improvements in the preparation of polymethylene polyphenyl polyisocyanates by phosgenation of a mixture of the corresponding polyamines.

2. Description of the Prior Art

This invention is based on the finding that the introduction of very minor amounts of water into the reaction mixture at a certain juncture in the manufacture of an organic polyisocyanate can produce dramatic improvements in certain properties of the resulting polyisocyanate. Previous attempts have been made to modify the properties of organic polyisocyanates by treating the isolated polyisocyanate with water. Illustratively, U.S. Pat. No. 3,526,652 describes the treatment of polymethylene polyphenyl polyisocyanates with from 0.1 to 0.5 percent by weight of water at elevated temperatures. The polyisocyanate so modified is said to give rise to polyurethane foams, by reaction with a polyol, which have increased flame retardant properties.

U.S. Pat. No. 3,179,680 describes the treatment of certain aromatic polyisocyanates with minor amounts of water in order to reduce the hydrolyzable chloride content. U.S. Pat. No. 3,636,030 describes treating the still residues, remaining after distillation of aromatic isocyanates, with aqueous hydrochloric or hydrobromic acid to achieve partial hydrolysis of various components therein and then phosgenating the product to obtain additional aromatic diisocyanate.

U.S. Pat. No. 4,221,877 describes heating methylenebis(phenyl isocyanate) with water in controlled amounts to form a polyisocyanate containing biurets. The resulting isocyanate is said to give flexible polyurethane foams, when reacted with the appropriate polyol, which foams have improved physical properties as compared with the corresponding foams made from the untreated diisocyanate.

U.S. Pat. No. 3,641,094 teaches the phosgenation of primary amines in the presence of aqueous alkali to obtain the corresponding isocyanates rapidly and with utilization of relatively small proportions of phosgene to amine.

We have found that, by treating polymethylene polyphenyl polyisocyanate and related polymeric isocyanates at a specific stage prior to isolation from the phosgenation reaction mixture employed in their preparation, it is possible to produce highly significant and advantageous changes in the properties of the polyisocyanates in question. One important improvement is a significant reduction in formation of dark colored material which generally occurs during isolation of the polyisocyanate from its reaction mixture. Equally important is the production of a product which has lower viscosity and contains significantly less higher molecular weight components than is normally encountered. All these improvements are of significant commerical importance.

SUMMARY OF THE INVENTION

This invention comprises an improved process for the preparation of polymethylene polyphenyl polyisocyanates by phosgenation of the corresponding mixture of polyamines in solution in an inert organic solvent followed by removal of excess phosgene and stripping of said solvent wherein the improvement comprises introducing into the reaction mixture, after completion of the phosgenation but prior to completion of removal of phosgene therefrom, from about 0.1 percent by weight to about 5 percent by weight of water, based on the amount of polyisocyanate present in the reaction mixture.

The process of the invention can be carried out on a continuous or semi-continuous basis as well as on a batch basis. The invention also comprises the polymethylene polyphenyl polyisocyanates prepared by the process of the invention.

DETAILED DESCRIPTION OF THE INVENTION

Polymethylene polyphenyl polyisocyanates are prepared commercially by phosgenation of the corresponding polyamines. The latter are prepared by condensation of formaldehyde and aromatic amines, especially aniline and or substituted anilines, generally in the presence of an acid catalyst; see, for example, U.S. Pat. Nos. 2,683,730; 2,950,263; 3,012,008; 3,097,191; and 3,260,751. The phosgenation is normally carried out in the presence of an inert organic solvent such as chlorobenzene, dichlorobenzene and the like. When the phosgenation has been completed, the excess phosgene is removed together with the inert organic solvent. Initially the phosgene which is present as vapor is vented from the reaction mixture, together with any hydrogen chloride which has been formed. The bulk of the phosgene is removed by distillation using various types of stripping vessels. The stripping is carried out at atmosphere pressure, or above or below atmospheric pressure, and the phosgene is readily separated from the solution of polyisocyanate in the inert solvent. Subsequently, the inert solvent is itself stripped using distillation, leaving the polyisocyanate as the final product. Advantageously, a part of the solvent is removed under pressure as described in U.S. Pat. No. 3,912,600.

The process of the invention is carried out by introducing water, in any of a variety of forms as discussed below, into the mixture either immediately prior to or during the stripping of the phosgene from the phosgenation reaction product. The only criticality is that the water must be added prior to removal of all of the phosgene. It is found that addition of water, even in the small amounts called for by the present invention, after all the phosgene has been removed does not produce the highly useful result discussed above. Certainly the addition of water after the polyisocyanate has been isolated from the reaction product does not give the desired effect.

The water can be introduced into the reaction product from which phosgene is being stripped using any of a wide variety of methods. Thus, water in liquid form can be introduced into the feedstock for the phosgene stripping process or can be introduced at some intermediate stage in the phosgene stripping process by suitable means. These means can include introduction of the water as a liquid, advantageously as a spray, into the feedstock or the product from which part of the phosgene has been stripped. If the stripping is part of a continuous production unit, the liquid water can be introduced as a spray on a continuous basis in the appropriate proportions based on the rate of throughput of the solution being stripped. The water can be introduced in the same manner but on a one-shot basis where the process is being operated on a batch basis. In the latter case it is also convenient to introduce the water in liquid form absorbed on a substrate such as a porous ceramic material, e.g. crushed brick and the like or any other porous substrate which is resistant to the chemically corrosive phosgenation reaction mixture. In an alternative method of introducing the water into the reaction mixture in accordance with the invention, the water can be introduced as steam or as droplets entrained in a stream of inert gas such as nitrogen and the like or in the form of a humidified inert gas. These methods of introduction can be utilized in both continuous and batch type operations.

The water can also be introduced in a chemically or physically bound form into the phosgenation product. For example, a tertiary alcohol such as tertiary butanol, which dissociates under the conditions prevailing in the phosgenation product to yield water and an olefin, can be employed as the source of the water required to accomplish the process of the invention. The tertiary alcohol can be introduced in liquid or vapor form using any of the procedures described above for the introduction of water as such. Methods of introducing water in bound form also include the use of inorganic salts containing water of crystallization which would be liberated under the conditions prevailing in the phosgenation product. Other methods of introducing water in bound form will be apparent to one skilled in the art.

Whatever method is adopted of introducing the water into the phosgenation reaction product, the amount introduced should lie within the range of about 0.1 percent by weight to about 5 percent by weight based on the total amount of isocyanate present in the reaction product and preferably within the range of about 0.5 to about 2 percent by weight based on the total amount of isocyanate.

The temperature of the phosgenation product at the time at which the water is introduced into the reaction mixture is advantageously within the range of about 0° C. to about 200° C. and preferably within the range of about 0° C. to about 125° C. After the water has been added it is advantageous to delay the stripping of phosgene from the resulting product for a period which can vary from about 2 minutes to about 60 minutes depending in part upon the form in which, and the method by which, the water has been introduced and on the temperature employed. The most appropriate residence time in any particular instance can be readily determined by a process of trial and error.

The temperature at which the phosgene is stripped from the reaction mixture can vary over a wide range depending on the pressure employed. Advantageously, the temperature at which the phosgene is stripped in the presence of the added water is within the range of about 100° C. to about 200° C. and preferably is in the range of about 125° C. to about 185° C. By operating at any of the temperatures within this range it is found that the resulting isocyanate has a significantly improved color, i.e. is much lighter in color than the dark brown products which have been obtained hitherto in the absence of the treatment called for by the present invention.

The process of the invention can be applied to the treatment of any of the polymethylene polyphenyl polyisocyanates known in the art. The term, polymethylene polyphenyl polyisocyanates, is applied generically to the product obtained by phosgenating the mixture of polyamines obtained by condensing aromatic amines and formaldehyde as described, for example, in the references cited above. Illustrative of aromatic amines which can be employed in the condensation are aniline, chloroaniline (m- and p-isomers), toluidine (o-, m- and p-isomers), phenetidine (o-, m- and p-isomers), anisidine (o-, m- and p-isomers), xylidine (o-, m- and p-isomers), 2,4-toluene diamine, 2,6-toluene diamine, and the like as well as mixtures of any two or more of said amines. The molar ratio in which the amine and formaldehyde are employed in such condensations, together with the amount and nature of the acid catalyst, are chiefly responsible for the composition of the resulting mixture of polyamines. As the proportion of aromatic amine to formaldehyde increases, the proportion of diamine, namely methylenebis-(aniline) in the case where the aromatic amine is aniline, which is present in the product, tends to increase. By modifying the conditions and molar ratios of the reactants in the condensation, it is possible to achieve products which contain the diamine in proportions as low as the order of 20 percent and as high as approximately 85 percent, the reminder of the mixture being triamines, tetramines and higher oligomers. When such mixtures of polyamines are phosgenated, they give rise to the corresponding mixture of polyisocyanates in substantially the same proportions of diisocyanate to tri-, tetra- and higher polyisocyanates as well as by-products (dimers and the like) some of which may be responsible for coloration. These mixtures are known generically as polymethylene polyphenyl polyisocyanates as discussed above.

The finding that the introduction of water in the manner described above can give the highly useful results reported herein is believed to be surprising and unexpected. It is believed to be particularly surprising to find that the useful changes in properties in the resulting polyisocyanate are only achieved if the water is added before all the phosgene has been removed from the reaction mixture and are not achieved if the water is added after all the phosgene has been removed.

The practical usefulness of Applicant's findings will be obvious to one skilled in the art. The reduction in viscosity facilitates the ease of handling of the product in the preparation of polyurethane products such as foams and the like. Further, the lighter color of the polyisocyanate gives rise to a much lighter color in the products (e.g. rigid polyurethane and polyisocyanurate foams) prepared therefrom and this is a significant consideration where the color of these ultimate products is readily apparent to the end user. Other practical advantages will be readily apparent to those skilled in the art.

The following examples describe the manner and process of making and using the invention and set forth the best mode contemplated by the inventor of carrying out the invention, but are not to be construed as limiting.

EXAMPLE 1

The feed polyisocyanate employed in the experiments described in this Example was a solution (about 10 percent by weight) of polymethylene polyphenyl polyisocyanate in chlorobenzene taken as an aliquot from a commercial plant phosgenation run prior to stripping all of the phosgene from the phosgenation reaction mixture. A portion of the material was retained as control and the other portion was subjected to treatment in accordance with the process of the invention as follows:

The feedstock (circa 3 liters) was charged to a 5-liter flask equipped with heating mantle, magnetic stirrer, overhead condenser and reflux head. A total of about 2000 g. of granulated DURO brand chemically resistant brick having an absorbed content of water of about 54 g. was placed on a Teflon support ring, prior to introduction of the feedstock, at a level at which it was submerged in the feedstock when the latter was charged to the flask. The feedstock was introduced to the flask at 25° C. and was maintained at that temperature for 15 minutes with stirring. At the end of this period the feedstock was heated and solvent was distilled at atmospheric pressure until the temperature of the mixture reached 150° C. at which point the mixture was heated under reflux for 1 hour. Thereafter the reaction mixture was distilled under vacuum and the residue was held at 180° C. in vacuo for 30 minutes to remove the last traces of solvent. The resulting polyisocyanate was subjected to analysis to determine its composition, viscosity, light absorption at 440 nm and 500 nm and also to determine its reactivity in the formation of polyurethane foam using a standard formulation as well as the degree of coloration (as measured by absorption of light at various frequencies) of the foam so prepared. In TABLE 1 below are recorded the results of two separate runs using different feed polyisocyanates. The corresponding composition and properties of the two control samples, subjected to exactly the same treatment but in the absence of the granulated brick, are given for purposes of comparison.

TABLE 1

| Test | Run A Control | Run A Brick treated | Run B Control | Run B Brick treated |
|---|---|---|---|---|
| [1]% Hot HCl | 0.07 | 0.05 | 0.08 | 0.04 |
| [1]% Hydrolyzable Cl | 0.07 | 0.05 | 0.09 | 0.05 |
| [1]% Total hydrolyzable Cl | 0.31 | 0.36 | 0.52 | 0.49 |
| Isocyanate equiv. | 134.8 | 134.4 | 134.8 | 134.2 |
| Viscosity at 25° C.: cps | 183 | 171 | 231 | 185 |
| [2]Composition: | | | | |
| % Diisocyanate | 43.9 | 45.5 | 44.6 | 46.3 |
| % Triisocyanate | 16.8 | 18.8 | 17.7 | 18.1 |
| % Tetra | 8.8 | 10.3 | 9.5 | 10.1 |
| % Penta | 5.9 | 6.1 | 5.4 | 5.9 |
| % Higher M. Wt. | 24.6 | 19.3 | 22.8 | 19.6 |
| Light absorption | | | | |
| at 440 nm. | 46.3 | 18.0 | 35.5 | 15.4 |
| 500 nm. | 11.9 | 4.7 | 7.7 | 4.0 |
| [3]Foam: | | | | |
| Cream time: min. | 1:10 | 0:57 | 1:12 | 0:47 |
| Gel time: min. | 2:21 | 2:00 | 3:15 | 2:27 |
| Rise time: min. | 2:57 | 2:38 | 4:11 | 3:03 |
| Foam light absorption | | | | |
| at 400 nm. | 0.530 | 0.395 | 0.555 | 0.304 |
| 440 nm. | 0.440 | 0.295 | 0.434 | 0.228 |
| 500 nm. | 0.286 | 0.164 | 0.250 | 0.120 |
| 600 nm. | 0.179 | 0.103 | 0.142 | 0.056 |
| 700 nm. | 0.116 | 0.065 | 0.075 | 0.023 |

Footnotes:
[1]Test procedure described in U.S. Pat. No. 3,793,362 at Col. 7, line 24 - Col. 8, line 12.
[2]By gel permeation chromatography.
[3]Determined using a standard foam rise time test procedure with the test polyisocyanate as the "A" side and System 977-C-455 (Cook Paint and Varnish Company) as the "B" side (mixture of polyols, silicone surfactant, fluorocarbon and catalyst).

It will be seen from the above data that, in the case of both Runs A and B, the polyisocyanate, after treatment in accordance with the invention, exhibited lower viscosity, higher diisocyanate content, lower content of higher molecular weight fractions, increased reactivity and lighter color than the corresponding control samples. In addition, the lighter color of the polyisocyanate was reflected in the lighter color of the polyurethane foams prepared therefrom.

EXAMPLE 2

The feedstocks employed in Runs C and D described below were both solutions of polymethylene polyphenyl polyisocyanate in chlorobenzene taken as aliquots from a commercial phosgenation run similar to that of Example 1 at the stage prior to stripping of the phosgene from the phosgenation reaction mixture. The procedure employed in the treatment of the feedstocks was exactly that described for Runs A and B in Example 1 except that, in Run C, the granulated DURO brick was dried prior to use by heating under vacuum and, in the controls for Runs C and D, approximately an equal volume of granulated non-porous glass brick was disposed on a Teflon support ring in the reaction mixture during treatment. It will be seen from the results shown in TABLE 2 below that the use of the dried DURO brick in Run C gave an isocyanate which exhibited no significant difference in properties compared with the control, whereas in Run D the use of the DURO brick which had not been dried (water content about 2.7% w/w) gave an isocyanate which exhibited lower viscosity, lighter color, higher diisocyanate content and lower content of higher molecular weight fractions than the control isocyanate. Further, the polyurethane foam prepared from the treated isocyanate exhibited significantly lighter color than that prepared from the control sample.

TABLE 2

| Test | Run C Control | Run C Brick treated (anhydrous) | Run D Control | Run D Brick treated |
|---|---|---|---|---|
| % Hot HCl | 0.03 | 0.02 | 0.03 | 0.02 |
| % Hydrolyzable Cl | 0.04 | 0.03 | 0.03 | 0.03 |
| % Total Hydrolyzable Cl | 0.39 | 0.34 | 0.32 | 0.33 |
| Isocyanate equiv. | 134.1 | 133.1 | 133.2 | 131.7 |
| Viscosity at 25° C.: cps | 102 | 98 | 138 | 97 |
| Composition: | | | | |
| % Diisocyanate | 49.3 | 49.6 | 45.1 | 47.6 |
| % Triisocyanate | 19.0 | 19.1 | 19.1 | 20.5 |
| % Tetra | 9.4 | 9.7 | 9.8 | 10.8 |
| % Penta | 6.0 | 5.5 | 6.2 | 6.6 |
| % Higher M.W. | 16.3 | 16.1 | 19.8 | 14.5 |
| Light absorption | | | | |
| at 440 nm. | 34.0 | 37.9 | 34.2 | 10.1 |
| 500 nm. | 7.3 | 7.8 | 6.0 | 2.2 |
| Foam: | | | | |
| Cream time: min. | 0:45 | 0:45 | 0:35 | 0:34 |
| Gel time: min. | 2:24 | 2:20 | 2:17 | 2:15 |
| Rise time: min. | 3:01 | 2:55 | 2:52 | 2:43 |
| Foam light absorption | | | | |
| at 400 nm. | 0.638 | 0.483 | 0.658 | 0.324 |
| 440 nm. | 0.520 | 0.365 | 0.525 | 0.233 |
| 500 nm. | 0.290 | 0.173 | 0.265 | 0.107 |
| 600 nm. | 0.162 | 0.087 | 0.150 | 0.065 |
| 700 nm. | 0.103 | 0.046 | 0.096 | 0.044 |

EXAMPLE 3

The experiment described for Run D in Example 2 was repeated exactly as described with the sole exception that the feedstock employed, which again was an aliquot taken from a commercial phosgenation run at the stage prior to stripping of the phosgene, had a significantly higher content (ca 67 percent w/w) of diisocyanate. The results are recorded in TABLE 3 below and it will be seen that the isocyanate which had been treated in accordance with the invention possessed slightly lower viscosity and significantly lower color than the control.

TABLE 3

|  | Run E | |
|---|---|---|
| Test | Control | Brick treated |
| % Hot HCl | 0.04 | 0.04 |
| % Hydrolyzable Cl | — | — |
| % Total Hydrolyzable Cl | 0.27 | 0.27 |
| Isocyanate equiv. | 132.7 | 132.3 |
| Viscosity at 25° C.: cps | 41 | 35 |
| Composition: | | |
| % Diisocyanate | 66.8 | 66.6 |
| % Triisocyanate | 12.7 | 13.0 |
| % Tetra | 5.7 | 6.3 |
| % Penta | 4.5 | 5.0 |
| % Higher M.W. | 10.3 | 9.1 |
| Light absorption | | |
| at 440 nm. | 30.3 | 3.6 |
| 500 nm. | 3.8 | 0 |
| Foam: | | |
| Cream time: min. | 0:44 | 0:47 |
| Gel time: min. | 2:10 | 2:07 |
| Rise time: min. | 2:51 | 2:46 |
| Foam light absorption | | |
| at 400 nm. | 0.597 | 0.255 |
| 440 nm. | 0.480 | 0.184 |
| 500 nm. | 0.289 | 0.112 |
| 600 nm. | 0.177 | 0.078 |
| 700 nm. | 0.125 | 0.054 |

EXAMPLE 4

Using different feedstocks, each taken as an aliquot from a commercial phosgenation run as described in Example 1, Runs F and G were carried out using the same apparatus and procedure described in Example 1 but omitting the DURO brick and adding water dropwise to the phosgenation feedstock prior to the start of the operation. In both cases the amount of water so added represented 0.5 percent w/w based on total isocyanate present. The controls in both runs were subjected to exactly the same treatment except that no water was added. The data generated in the two runs is shown in TABLE 4 from which it will be seen that the isocyanates produced in accordance with the invention exhibited lower viscosity and lighter color than the control isocyanates.

TABLE 4

|  | Run F | | Run G | |
|---|---|---|---|---|
| Test | Control | Water treated | Control | Water treated |
| % Hot HCl | 0.05 | 0.05 | 0.04 | 0.06 |
| % Hydrolyzable Cl | 0.06 | 0.06 | | |
| % Total Hydrolyzable Cl | 0.39 | 0.45 | 0.44 | 0.46 |
| Isocyanate equiv. | 131.6 | 130.7 | 132.5 | 132.3 |
| Viscosity at 25° C.: cps | 133 | 106 | 253 | 218 |
| Composition: | | | | |
| % Diisocyanate | 46.3 | 46.8 | 37.3 | 38.4 |
| % Triisocyanate | 19.2 | 20.2 | 22.4 | 22.3 |
| % Tetra | 10.7 | 11.3 | 11.6 | 11.5 |
| % Penta | 5.7 | 6.4 | 6.4 | 7.2 |
| % High M.W. | 17.6 | 15.3 | 22.3 | 20.6 |
| Light absorption | | | | |
| at 440 nm. | 28.3 | 10.4 | 24.6 | 5.2 |
| 500 nm. | 6.1 | 3.3 | 5.7 | 2.8 |
| Foam: | | | | |
| Cream time: min. | 1:00 | 0:49 | 0:54 | 0:58 |
| Gel time: min. | 2:43 | 2:16 | 2:36 | 2:36 |
| Rise time: min. | 3:26 | 2:49 | 3:24 | 3:15 |
| Foam light absorption | | | | |
| at 400 nm. | 0.690 | 0.640 | 0.460 | 0.337 |
| 440 nm. | 0.595 | 0.500 | 0.348 | 0.240 |
| 500 nm. | 0.370 | 0.339 | 0.208 | 0.160 |
| 600 nm. | 0.224 | 0.239 | 0.127 | 0.140 |
| 700 nm. | 0.151 | 0.187 | 0.088 | 0.103 |

EXAMPLE 5

Using the same feedstock polyisocyanate, which had been taken as an aliquot from a commercial phosgenation run at the stage prior to stripping of the phosgene, a series of runs were carried out using exactly the procedure employed in Runs F and G but adjusting the amount of water to be 0.25 percent w/w, 1 percent w/w, 2 percent w/w and 5 percent w/w. The data generated is shown in TABLE 5 below together with the data for the control isocyanate which was obtained using the identical procedure but without the addition of the water. It will be seen that the polyisocyanate obtained in each of the runs in which water was added exhibited lower viscosity, lighter color and lower content of higher molecular weight fractions than the control sample.

TABLE 5

| Test | Control | Run H (0.25% H2O) | Run I (1% H2O) | Run J (2% H2O) | Run K (5% H2O) |
|---|---|---|---|---|---|
| % Hot HCl | 0.03 | 0.05 | 0.05 | 0.06 | 0.05 |
| % Hydrolyzable Cl | | 0.05 | 0.05 | | |
| % Total Hydrolyzable Cl | 0.38 | 0.43 | 0.43 | 0.44 | 0.43 |
| Isocyanate equiv. | 131.3 | 132.1 | 131.4 | 132.0 | 132.5 |
| Viscosity at 25° C.: cps | 209 | 189 | 170 | 176 | 177 |
| Composition: | | | | | |
| % Diisocyanate | 39.0 | 40.4 | 41.0 | 41.6 | 40.4 |
| % Triisocyanate | 22.4 | 22.3 | 22.1 | 22.0 | 22.3 |
| % Tetra | 11.8 | 11.7 | 11.9 | 11.8 | 11.6 |
| % Penta | 6.7 | 7.1 | 7.0 | 7.1 | 7.2 |
| % Higher M.W. | 20.1 | 18.5 | 18.0 | 17.5 | 18.5 |
| Light absorption | | | | | |
| at 440 nm. | 28.8 | 11.2 | 6.3 | 6.9 | 5.9 |
| 500 nm. | 5.6 | 3.6 | 2.8 | 2.4 | 0.9 |

TABLE 5-continued

| Test | Control | Run H (0.25% H₂O) | Run I (1% H₂O) | Run J (2% H₂O) | Run K (5% H₂O) |
|---|---|---|---|---|---|
| Foam light absorption | | | | | |
| at 400 nm. | 0.550 | 0.380 | 0.267 | N.T. | N.T. |
| 440 nm. | 0.415 | 0.260 | 0.177 | N.T. | N.T. |
| 500 nm. | 0.225 | 0.152 | 0.104 | N.T. | N.T. |
| 600 nm. | 0.117 | 0.102 | 0.077 | N.T. | N.T. |
| 700 nm. | 0.077 | 0.066 | 0.053 | N.T. | N.T. |

EXAMPLE 6

Using different feedstocks, each of which had been taken as an aliquot from commercial phosgenation runs at a stage prior to stripping of the phosgene, two runs were carried out using exactly the procedure employed in Example 4 (Runs F and G) except that the water (at a level of 0.5 percent w/w based on total feedstock) was introduced as vapor using a stream of nitrogen saturated with water rather than being added dropwise in liquid form. The addition of the water in this manner was carried out prior to the start of the phosgene stripping operation. The data for the two runs is set forth in TABLE 6 below together with the corresponding control runs carried out using the same procedure but without the addition of the water. It will be seen from the data that the two polyisocyanates produced using the process of the invention were significantly lower in viscosity and lighter in color than the control samples.

TABLE 6

| | Run L | | Run M | |
|---|---|---|---|---|
| Test | Control | H₂O treated | Control | H₂O treated |
| % Hot HCl | 0.03 | 0.03 | 0.03 | 0.06 |
| % Hydrolyzable Cl | | | | |
| % Total Hydrolyzable Cl | 0.36 | 0.32 | 0.38 | 0.40 |
| Isocyanate equiv. | 131.9 | 132.7 | 131.3 | 132.3 |
| Viscosity at 25° C.: cps | 135 | 115 | 209 | 187 |
| Composition | | | | |
| % Diisocyanate | 43.7 | 44.5 | 39.0 | 39.7 |
| % Triisocyanate | 19.5 | 19.1 | 22.4 | 22.3 |
| % Tetra | 10.6 | 11.0 | 11.8 | 11.8 |
| % Penta | 5.9 | 6.2 | 6.7 | 6.4 |
| % Higher M.W. | 20.3 | 19.2 | 20.1 | 19.8 |
| Light absorption | | | | |
| at 440 nm. | 28.2 | 4.8 | 28.8 | 8.5 |
| 500 nm. | 6.0 | 2.3 | 5.6 | 3.0 |
| Foam: | | | | |
| Cream time: min. | 1:14 | 1:10 | N.T. | |
| Gel time: min. | 2:36 | 2:24 | | |
| Rise time: min. | 3:12 | 2:57 | | |
| Foam light absorption | | | | |
| at 400 nm. | 0.478 | 0.315 | N.T. | |
| 440 nm. | 0.340 | 0.205 | | |
| 500 nm. | 0.173 | 0.104 | | |
| 600 nm. | 0.084 | 0.065 | | |
| 700 nm. | 0.047 | 0.045 | | |

EXAMPLE 7 (COMPARISON EXAMPLE)

For purposes of comparison the Run A described in Example 1 was repeated but the feedstock polyisocyanate there used was replaced by an aliquot of a polyisocyanate taken from a commercial phosgenation run after the phosgene stripping was completed but before removal of the chlorobenzene solvent. The data shown in TABLE 7 was obtained in respect of the properties of the polyisocyanate so treated together with the corresponding data for a control sample from the same aliquot and treated in exactly the same manner but without the use of the DURO brick. It will be seen that there was no significant difference in any of the properties of the treated material and the control.

TABLE 7

| | Run N | |
|---|---|---|
| Test | Control | Brick treated |
| % Hot HCl | 0.04 | 0.02 |
| % Hydrolyzable Cl | 0.04 | 0.02 |
| % Total Hydrolyzable Cl | 0.20 | 0.16 |
| Isocyanate equiv. | 131.6 | 131.5 |
| Viscosity at 25° C.: cps | 29 | 30 |
| Composition: | | |
| % Diisocyanate | 71.1 | 70.0 |
| % Triisocyanate | 12.7 | 12.2 |
| % Tetra | 5.2 | 5.4 |
| % Penta | 4.0 | 4.1 |
| % Higher M.W. | 7.0 | 8.3 |
| Light absorption | | |
| at 440 nm. | 30.4 | 25.6 |
| 500 nm. | 8.2 | 8.6 |
| Foam | | |
| Cream time: min. | 0:54 | 0:54 |
| Gel time: min. | 2:11 | 2:03 |
| Rise time: min. | 2:45 | 2:36 |
| Foam light absorption | | |
| at 400 nm. | 0.455 | 0.466 |
| 440 nm. | 0.366 | 0.381 |
| 500 nm. | 0.233 | 0.251 |
| 600 nm. | 0.118 | 0.127 |
| 700 nm. | 0.060 | 0.070 |

EXAMPLE 8 (COMPARISON EXAMPLE)

This Example illustrates the effect of adding water to a polyisocyanate after removal of phosgene and chlorobenzene solvent in accordance with prior art procedures. The feedstock employed was an aliquot of the final polymethylene polyphenyl polyisocyanate isolated from a commercial phosgenation process. The feedstock was subjected to the treatment described in Example 4, Runs F and G, using water at a level of 0.5 percent by weight based on isocyanate present. The properties of the polyisocyanate so treated, as well as those of a control sample subjected to exactly the same treatment but without the addition of water, are summarized in TABLE 8. It will be seen that the treatment *increased* the viscosity of polyisocyanate but did not change color or any other property in any significant manner.

TABLE 8

| | Run O | |
|---|---|---|
| Test | Control | H₂O treated |
| % Hot HCl | 0.04 | 0.03 |
| % Hydrolyzable Cl | 0.04 | 0.04 |
| % Total Hydrolyzable Cl | 0.46 | 0.43 |
| Isocyanate equiv. | 134.3 | 135.9 |
| Viscosity at 25° C.: cps | 173 | 224 |
| Composition: | | |
| % Diisocyanate | 45.3 | 44.0 |

TABLE 8-continued

| Test | Run O | |
|---|---|---|
| | Control | H₂O treated |
| % Triisocyanate | 17.6 | 16.9 |
| % Tetra | 9.1 | 8.5 |
| % Penta | 5.8 | 5.0 |
| % Higher M.W. | 22.2 | 25.1 |
| Light absorption | | |
| at 440 nm. | 65.5 | 61.8 |
| 500 nm. | 15.8 | 15.7 |
| Foam: | | |
| Cream time: min. | 1:05 | 1:07 |
| Gel time: min. | 2:24 | 2:25 |
| Rise time: min. | 3:01 | 3:01 |
| Foam light absorption | | |
| at 400 nm. | 0.590 | 0.590 |
| 440 nm. | 0.465 | 0.470 |
| 500 nm. | 0.260 | 0.273 |
| 600 nm. | 0.142 | 0.149 |
| 700 nm. | 0.083 | 0.084 |

EXAMPLE 9

An aliquot was taken, at the stage prior to phosgene stripping, from a commercial phosgenation run for the production of polymethylene polyphenyl polyisocyanate. A portion of the aliquot was treated dropwise with t-butanol in an amount representing 2% w/w based on feedstock and then subjected to the procedure described in Example 1 but omitting the DURO brick. A second portion (control sample) of the aliquot was treated in exactly the same manner except that no t-butanol was added. The data generated in the two runs is shown in TABLE 9. It will be seen that the isocyanate produced using the t-butanol treatment exhibited lighter color than the control sample although, in contrast to the runs described in previous examples, the viscosity had increased and so had the isocyanate equivalent. It is believed that the increase in viscosity and isocyanate equivalent is probably due to incomplete dissociation of the t-butanol (to yield water and isobutylene) prior to removal of all phosgene from the reaction mixture. If all the t-butanol dissociated, the amount of water generated in the reaction mixture would be 0.49% w/w.

TABLE 9

| Test | Control | t-butanol treated |
|---|---|---|
| % Hot HCl | 0.05 | 0.04 |
| % Hydrolyzable Cl | 0.05 | 0.04 |
| % Total Hydrolyzable Cl | 0.40 | 0.33 |
| Isocyanate equiv. | 132.7 | 137.0 |
| Viscosity at 25° C.: cps | 219 | 503 |
| Composition: | | |
| % Diisocyanate | 38.0 | 35.3 |
| % Triisocyanate | 21.4 | 19.4 |

TABLE 9-continued

| Test | Control | t-butanol treated |
|---|---|---|
| % Tetra | 11.3 | 10.2 |
| % Penta | 6.6 | 5.9 |
| % Higher M.W. | 22.7 | 29.2 |
| Light absorption | | |
| at 440 nm. | 26.0 | 19.5 |
| 500 nm. | 5.7 | 3.2 |
| Foam | | |
| Cream time: min. | 1:03 | 1:01 |
| Gel time: min. | 2:40 | 2:42 |
| Rise time: min. | 3:15 | 3:18 |

I claim:

1. In a process for the preparation of polymethylene polyphenyl polyisocyanates by phosgenation of the corresponding polyamines in solution in an inert organic solvent followed by removal of excess phosgene and stripping of said solvent the improvement which comprises introducing into the reaction mixture, after completion of the phosgenation but prior to completion of removal of phosgene therefrom, from about 0.1 percent by weight to about 5 percent by weight of water, based on polyisocyanate present in the reaction mixture.

2. A process according to claim 1 wherein the water is introduced prior to removal of the major portion of the phosgene from the reaction mixture.

3. A process according to claim 1 wherein the amount of water introduced into the reaction mixture is within the range of about 0.5 to about 2 percent by weight based on polyisocyanate present in the reaction mixture.

4. A process according to claim 1 wherein the water is introduced into the reaction mixture by contacting the latter with water absorbed on a porous substrate.

5. A process according to claim 4 wherein said porous substrate is an inert inorganic material.

6. A process according to claim 1 wherein the water is directly dispensed into the reaction mixture in liquid form.

7. A process according to claim 1 wherein the water is introduced into the reaction mixture in the form of steam.

8. A process according to claim 1 wherein the water is introduced into the reaction mixture by entrainment in an inert gas.

9. A process according to claim 1 wherein the water is generated in situ by introducing a tertiary aliphatic alcohol into the reaction mixture in an amount sufficient to generate an amount of water falling within the range set forth in said claim 1.

10. A process according to claim 9 wherein the tertiary aliphatic alcohol is tertiary butanol.

11. A process according to claim 1 wherein the reaction mixture is held at a temperature within the range of about 0° C. to about 200° C. for a period of at least 2 minutes after addition of the water has been completed.

* * * * *

UNITED STATES PATENT OFFICE
CERTIFICATE OF CORRECTION

Patent No. 4,465,639　　　　　　　　Dated August 14, 1984

Inventor(s) Richard Hatfield, Jr.

It is certified that error appears in the above-identified patent and that said Letters Patent are hereby corrected as shown below:

Column 2, line 35 "atmosphere" should read --atmospheric--.
Column 4, line 15 "methylenebis-(aniline)" should read --methylenebis(aniline)--; line 22 "reminder" should read --remainder--.  Column 5, line 17 "in vacuo" should read --in vacuo--.  Column 9, Table 6, line 49, the "N.T." at "Cream time: min." under "Run M" should be at "Gel time: min." under "Run M"; Table 6, line 52, the "N.T." at "400 nm." under "Run M" should be at "440 nm." under "Run M"; line 64 "after" should read --after--.
Column 12, Claim 9, line 47 "in situ" should read --in situ--.

Signed and Sealed this

Seventh Day of May 1985

[SEAL]

Attest:

DONALD J. QUIGG

Attesting Officer　　　Acting Commissioner of Patents and Trademarks